United States Patent [19]

Stüber et al.

[11] Patent Number: 5,571,844

[45] Date of Patent: Nov. 5, 1996

[54] AMIDINOPHENYLALANINE DERIVATIVES, A PROCESS FOR THEIR PREPARATION, THEIR USE AND COMPOSITIONS CONTAINING THESE AS ANTICOAGULANTS

[75] Inventors: Werner Stüber, Lahntal 3; Rainer Koschinsky, Cölbe, both of Germany

[73] Assignee: Behringwerke Aktiengesellschaft, Marburg, Germany

[21] Appl. No.: 354,741

[22] Filed: Dec. 8, 1994

[30] Foreign Application Priority Data

Dec. 10, 1993 [DE] Germany ............... 43 42 154.7

[51] Int. Cl.⁶ ..................................... A61K 31/18
[52] U.S. Cl. ............... 514/602; 514/54; 514/319; 514/330; 514/456; 514/604; 514/622; 546/205; 546/206; 546/226; 564/85; 564/89; 564/92; 549/399; 549/400; 549/401
[58] Field of Search .................. 546/226, 205, 546/206; 564/85, 89, 92; 549/399, 400, 401; 514/54, 319, 330, 456, 602, 604, 822

[56] References Cited

U.S. PATENT DOCUMENTS

| | | | |
|---|---|---|---|
| 4,093,712 | 6/1978 | Okamoto et al. | 424/177 |
| 4,791,102 | 12/1988 | Bernat et al. | 514/19 |
| 5,274,098 | 12/1993 | Stuer et al. | 546/226 |

FOREIGN PATENT DOCUMENTS

| | | |
|---|---|---|
| 0154432 | 9/1985 | European Pat. Off. |
| 0508220A1 | 10/1992 | European Pat. Off. |
| 0513543A1 | 11/1992 | European Pat. Off. |
| 0558961A2 | 9/1993 | European Pat. Off. |
| 2593813 | 8/1987 | France . |
| 2247239 | 2/1992 | United Kingdom . |

OTHER PUBLICATIONS

Eur. Polym. J. vol. 19, No. 12, pp. 1177–1183 (1983).

Yi-An Lu et al., "Pegylated Peptides I: Solid–Phase Synthesis of N a–Pegylated Peptides Using Fmoc Strategy," Peptide Research, 6:3(1993).

*Primary Examiner*—Brian M. Burn
*Attorney, Agent, or Firm*—Finnegan, Henderson, Farabow, Garrett & Dunner, L.L.P.

[57] ABSTRACT

The invention relates to amidinophenylalanine derivatives, to the synthesis of these compounds, to their use and to pharmaceutical compositions which contain these compounds which act as thrombin inhibitors.

11 Claims, No Drawings

AMIDINOPHENYLALANINE DERIVATIVES, A PROCESS FOR THEIR PREPARATION, THEIR USE AND COMPOSITIONS CONTAINING THESE AS ANTICOAGULANTS

The invention relates to amidinophenylalanine derivatives, to the synthesis of these compounds, to their use and to pharmaceutical compositions which contain these compounds which act as thrombin inhibitors.

As shown in EP-A-0 508 220 and 0 513 543, amidinophenylalanine derivatives can be used to have a beneficial effect on the pathological process of a thrombosis by inhibition of thrombin. However, for medical use of such compounds it is often desirable to prolong the retention time in the human body.

This invention is therefore based on the object of finding novel derivatives of amidinophenylalanine which have a prolonged retention time in the body of warm-blooded animals.

Surprisingly, it has been possible to achieve the object by binding derivatives of amidinophenylalanine to polymeric substances.

Examples of suitable derivatives of amidinophenylalanine are those described in EP-A-0 508 220 and 0 513 543.

Suitable polymers are physiologically tolerated substances which are preferably covalently bonded to the substances with inhibitory activity. Such polymers are preferably polyethylene glycols (PEG) with a molecular weight of about 750–30000, preferably 750–20000, or polysaccharides such as dextrans with a molecular weight of 20000–75000, heparins with a molecular weight of 2000–30000 or gelatin partial hydrolysates which may also, where appropriate, be crosslinked (polygeline).

Compounds according to the invention are also those with insoluble polymers. These include, for example, agarose derivatives such as, for example, Sepharoses, celluloses, or copolymers based on acrylic acid, which may, for example, contain polyethylene glycol and be crosslinked with crosslinkers such as divinylbenzene.

Accordingly, the invention relates to substances of the formula I

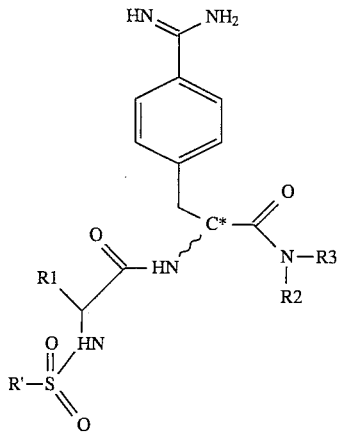

in which

R' is a naphthalene ring which is bonded in the alpha or beta position and is optionally derivatized with alkyl groups which contain up to 3 carbon atoms and/or alkoxy groups having up to 3 carbon atoms in each case, or is a tetralin ring which is bonded in the-alpha or beta position and is optionally derivatized with alkyl groups which contain up to 3 carbon atoms and/or alkoxy groups having up to 3 carbon atoms in each case, or is a phenyl ring which is optionally derivatized with alkyl groups which contain up to 4 carbon atoms, and/or with up to three groups of the structure Z-X in which O is oxygen or sulfur and X is hydrogen, methyl, ethyl, n-propyl, i-propyl or tert-butyl, is a chroman system which is derivatized preferably with up to 5 alkyl groups which contain up to 3 carbon atoms, R1 is a group of the structure A-B-poly in which A is —(CH$_2$)$_n$—, n is an integer from 1 to 7, B is a bond, —CO—NH—, N(Y)—CO —with Y=H, CH$_3$ or C$_2$H$_5$, —CO—O—, —O—CO—, —SO$_2$—NH—, —S—S—, —S—, —O —or —N(Y) —with Y=H, CH$_3$ or C$_2$H$_5$ and poly is a polymer from the group of polyethylene glycols or of polysaccharides, a gelatin partial hydrolysate which can also optionally be crosslinked, or a copolymer of acrylic acid and polyethylene glycol with a crosslinker, and this polymer has a molecular weight of up to 75000, and R2 and R3 can be identical or different and are an alkyl group with up to 4 carbon atoms or together form a ring and may possibly be derivatized with a hydroxyl group or a hydroxyalkyl group, where the hydroxyalkyl group contains up to 3 carbon atoms, and this hydroxyl group is optionally also in esterified form, where the appropriate acids are carboxylic acids which preferably contain up to 17 carbon atoms, and their physiologically acceptable salts and C* is in the R or S structure, but preferably in the R structure.

In more detail and without restriction to the following examples, groups suitable and preferred as R' are the following:

| | |
|---|---|
| 6,7-dimethoxynaphthyl | (β-Dmn) |
| 5-methoxynaphthyl | (β-Mns) |
| 2,2,5,7,8-pentamethylchromanyl | (PMC) |
| 5,6,7,8-tetrahydronaphthyl | (Thn) |
| 5,6,7,8-tetramethylnaphthyl | (Tmn) |
| phenyl | (Phl) |
| 4-methoxy-2,3,5-trimethylphenyl | (Mtr) |
| 2,3,4,5,6-pentamethylphenyl | (Pme) |
| 4-methoxy-2,3,5,6-tetramethylphenyl | (Mte) and |
| 4-hydroxy-2,3,6-trimethylphenyl | (Htr) | n is preferably 1, 2 or 3.

Polyethylene glycols (PEG) are preferably used as polymers.

B is preferably —CO—NH—. This means that a polymer with an amino functionality is coupled to the group R1 with —CH$_2$—COOH. Such coupling reactions are known from the literature. For example, a coupling reaction with a carbodiimide is used for this purpose. Polymers containing amino groups, for example amino-PEG of the structure NH$_2$—CH$_2$—CH$_2$—PEG—OCH$_3$ (MW 750-20000) are commercially obtainable (RAPP POLYMERE, T ÜBINGEN). On the other hand, it is also possible to bond a polymer via a carboxyl group to an amino group on the remainder of the molecule (Group B =—NH—CO—). For this purpose, for example, a polymer with the structure CH$_3$O—PEG—CH$_2$—CH$_2$—NH—CO—CH$_2$—CH$_2$—COOH is bonded to the side chain R1 =—(CH$_2$)$_n$—N(Y)H where n and Y have the abovementioned meaning. Furthermore, polymers of the structure CH$_3$O—PEG—CH$_2$—CH$_2$—Br or CH$_3$O—PEG—CH$_2$—CH$_2$—SH can be reacted with compounds of the formula I in which R1 is W—(CH$_2$)$_n$— with W =SH, OH or NH(Y) and n is as indicated for formula I to give compounds according to the invention with B being S, O or N(Y) with Y =H, CH$_3$ or C$_2$H$_5$, or S—S.

If hydroxyl functionalities are present on the radicals R2 or R3, these can optionally be esterified with carboxylic acids. Examples of such carboxylic acids are acetic acid, succinic acid, hexanecarboxylic acid, octanecarboxylic acid, decanecarboxylic acid, dodecanecarboxylic acid or hexadecanecarboxylic acid.

Since the amidino functionality is, by reason of the basic action, as a rule in the form of a salt, the thrombin inhibitors according to the invention can also occur in various salt forms. The salt form moreover has a considerable effect on the solubility of the compounds and on the absorbability in the case of therapeutic use. Salt forms which may be mentioned are formates, acetates, caproates or oleates, that is to say carboxylic acids with up to 16 carbon atoms, chlorides, bromides, iodides, alkanesulfonates with up to 10 carbon atoms, salts of dicarboxylic acids or tricarboxylic acids such as citrates or tartrates.

The invention also relates to the preparation of the polymer-bound compounds. Preferably, an amino acid derivative of the formula II

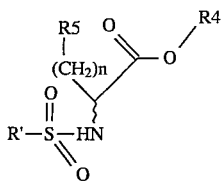

where R' and n have the above meaning, and R4 is a protective group customary in amino acid chemistry, for example a benzyl group, a tert-butyl group or a methyl group, and R5 is a carboxyl group or an amino group, a hydroxyl group, an SO$_3$H group or a sulfhydryl group (—SH), is reacted with an abovementioned polymer. The preparation takes place by reaction routes known per se and leads, after elimination of the protective group R4, to a polymer-bound amino acid derivative of the formula II in which R5 is a group polymer—B—, R4 is hydrogen and R', n and B have the abovementioned meaning. This polymer-bound amino acid is bound by known coupling methods, for example using dicyclohexylcarbodiimide in the solvent dimethylformamide, to the primary amino group of a compound of the formula III

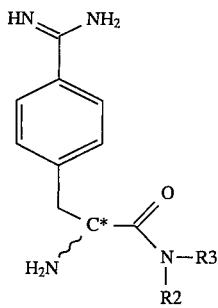

and thus a substance according to the invention is obtained.

The substances according to the invention are valuable thrombin inhibitors which are particularly distinguished in that they have a prolonged half-life in plasma. These substances are also very valuable because they show, for example on subcutaneous administration, a slow rise in their concentration in the plasma. Together with a longer half-life, overall a distinctly prolonged antithrombotic effect is achieved.

According to the teaching in PEPTIDE RESEARCH Vol. 6 No. 3, 140–146 (1993), the skilled worker would expect from such polymer-supported compounds that the ability to bind to thrombin, expressed by the Ki value, will be reduced. Surprisingly, however, the power of the inhibitors is significantly increased by attachment of the polymer carriers.

It is likewise surprising that the tolerability of the compounds according to the invention is improved by the attachment of the polymer.

The inhibitors according to the invention have been tested according to various criteria to assess their efficacy, these preferably being the determination of the Ki value, of the IC$_{50}$ value and of the partial thrombo-plastin time (PTT) in vivo and in vitro. To test the specificity, the IC$_{50}$ values and Ki values with respect to various serine proteases, especially thrombin and trypsin, were measured. The stability of the substances according to the invention was determined by incubating a sample of the substance with a pure enzyme, preferably trypsin, chymotrypsin or papain, and with liver or intestinal homogenates, taking samples from the solutions at intervals of time, and preferably measuring by HPLC.

The claimed compounds are specific and highly active thrombin inhibitors with a considerable antithrombotic potential which exceeds the previously known low molecular weight inhibitors in respect of duration of action and efficacy.

Abbreviations
Aph Amidinophenylalanine
NAPAP β-Naphthylsulfonylglycyl -D,L-p-amidinophenylalanyl piperidide
Asp Aspartic acid
Asn Asparagine
Glu Glutamic acid
Cys(SO$_3$H) Cysteinesulfonic acid
β-Dmn 6,7-Dimethoxynaphthyl
β-Mns 5-Methoxynaphthyl
Pmc 2,2,5,7,8-Pentamethylchromanyl
Thn 5,6,7,8-Tetrahydronaphthyl
Tmn 5,6,7,8-Tetramethylnaphthyl
Phl Phenyl
Mtr 4-Methoxy-2,3,6-trimethylphenyl
Pme 2,3,4,5,6-Pentamethylphenyl
Mte 4-Methoxy-2,3,5,6-tetramethylphenyl
Htr 4-Hydroxy-2,3,6-trimethylphenyl
Cph 4-Carboxyphenyl
z(Cbo) Benzyloxycarbonyl
Boc tert-Butyloxycarbonyl
Fmoc Fluorenylmethyloxycarbonyl
Pip Piperidine
OtBu tert-butyl ester
OMe Methyl ester
OEt Ethyl ester
OiBu iso-Butyl ester (sec-butyl ester)
OiPr iso-Propyl ester
TLC Thin-layer chromatography
DCCl Dicyclohexylcarbodiimide
DMF Dimethylformamide
FAB-MS Fast atom bombardment mass spectrometry
TOTU O-[(Cyano(ethoxycarbonyl)methylidene)amino]-1,1,3,3-tetramethyluronium tetrafluoroborate
DIPEA N-Ethyldiisopropylamine The following examples describe the invention in more detail:

EXAMPLE 1

4-Methoxy-2,3,6-trimethylphenylsulfonyl-L-Asp(PEG5000)- D-p-amidinophenylalanyl piperidide 1) 4-Methoxy-2,3,6-trimethylphenylsulfonyl-L-Asp-(PEG5000)-OH A) 4 g of amino-PEG 5000 monomethyl ether were dissolved with 400 mg (1 mmol) of 4-methoxy-2,3,6-trimethylphenyl- sulfonyl-L-Asp α-tert-butyl ester in 200 ml of DMF. To this were added, while stirring and cooling at 0° C., 328 mg (1 mmol) of TOTU as solid substance and subsequently 0.2 ml of DIPEA. The mixture was stirred at 0° C. for 1 h and at room temperature for 15 h. The solvent was removed in a rotary evaporator and the residue was then extracted by stirring several times with ethyl acetate, dissolved in warm methanol and crystallized using diethyl ether. The substance was filtered off with suction and dried and then used in this form for the next reaction.

B) The 4-methoxy-2,3,6-trimethylphenylsulfonyl-L-Asp(PEG5000)α-tert -butyl ester prepared in A) was stirred in 100 ml of a solution of 2N HCl in acetic acid, resulting in a clear solution. The solvent was then stripped off in vacuo, and adherent traces of acid were evaporated off in vacuo using toluene. The product was reprecipitated from methanol/diethyl ether and, after drying, obtained in the form of a white solid.

Yield: 2.8 g

Purity check: TLC

Rf =0.7 (butanol/glacial acetic acid/pyridine/water 4/1/1/2)

Rotation: $[\alpha]_D^{20}$ –1.8 (c =1, methanol)

Melting point: 57 ° C.

2) 4 -Methoxy-2,3,6 -trimethylphenylsulfonyl-L-Asp(PEG5000)- D-4-aminidinophenylalanyl piperidide 1.5 g of 4-methoxy-2,3,6-trimethylphenylsulfonyl-L-Asp(PEG5000)-OH were dissolved with 100 mg of D-4-amidino-phenylalanyl piperidide in 50 ml of DMF. The solution was cooled to 0° C. and then, with stirring, 100 mg of TOTU followed by 0.11 ml of DIPEA were added. After one hour at 0° C. the mixture was kept at room temperature for one hour and subsequently the solvent was removed in a rotary evaporator. The residue was dissolved in water and extracted by shaking 3 times with ethyl acetate, the aqueous phase was lyophilized and the lyophilizate was chromatographed in methanol on Sephadex®LH20.

Yield: 1.2 g

Purity check: TLC

Rf =0.5 (chloroform/methanol/glacial acetic acid 50/10/2.5) $^{13}$C NMR: (CD$_3$OD): 12.3, 18.4, 25.3, 26.6, 27.4, 30.5, 39.2, 40.4, 44.4, 51.1, 54.5, 56.3, 57.8, 71.6 (large), 113.47, 126.3, 128.0, 129.1, 130.5, 131.8, 140.2, 145.1, 160.9, 167.9, 169.6, 17 1.71

Determination of the Inhibition Constants for Thrombin

The inhibition constants (Ki) for the substances were determined by known enzyme kinetic methods. The human thrombin employed was determined to be 87% pure by means of active site titration. The assay solution for the Ki determination comprised buffer (50 mM tris-HCl, 75 mM NaCl, pH 7.8, 37 degrees C.),100 pM thrombin, 0.1 nM substrate S2238 (Kabi) and inhibitor, which covered a range from 0 to 0.2 nM. The inhibitor and enzyme were preincubated for 60 minutes, and the reaction was started by addition of the chromogenic substrate S2238. The kinetics were analyzed using the mathematical algorithm for tight binding, which with the aid of non-linear regression yielded Ki values (table) and the type of inhibition. The type of inhibition was found to be competitive for all the inhibitors.

TABLE

| SUBSTANCE | Ki [nM] Thrombin | Ki [nM] Trypsin | $t_{1/2}\beta$ [min] |
|---|---|---|---|
| Mtr—Asp(PEG5000)—Aph—Pip (1) | 0.3 | 387 | * |
| Mtr—Asp(PEG5000)—Aph—Pip (2) | 0.4 | 585 | 33 |
| Mtr—Asp(PEG10000)—Aph—Pip (3) | 0.6 | 1500 | 63 |
| Mtr—Asp(PEG20000)—Aph—Pip (4) | 0.6 | 941 | 74 |
| Mtr—Asp—Aph—Pip (5) | 2.5 | 312 | 19 |

*not assayed

Determination of the Specificity of the Inhibitors

The specificity of the inhibitors was determined with thrombin and trypsin. The specificity is defined as the ratio of the Ki values for trypsin and thrombin (table).

Determination of the Elimination Half-lives $t_{1/2}\beta$ The thrombin inhibitors (2)–(5) in the table were administered intravenously to rats (5 in each group) at a dosage of 5 mg/kg. Blood samples were taken, and the time-dependent concentrations of thrombin inhibitors in the plasma were determined. Elimination takes place in two phases. The calculated elimination half-lives $t_{1/2}\beta$ are compiled in it.

Determination of the Subcutaneous Absorption of Substances (2 ) and (5 )

The substances were administered to rabbits subcutaneously in a dosage of 2 mg/kg. The maximum plasma concentration of (5) was reached after 5 minutes. The maximum plasma concentration of (2) was reached after 80 minutes. (2 ) showed an effective plasma level over 6 hours, (5) over 3 hours.

We claim:

1. A compound of the formula 1

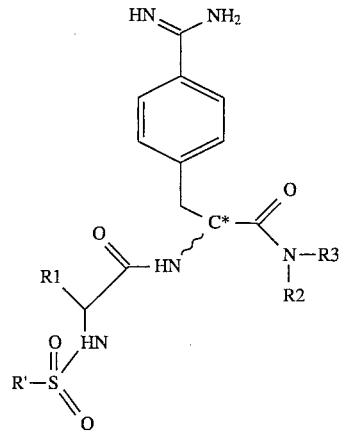

in which

R' is selected from the group consisting of a naphthalene ring which is bonded in the alpha or beta position and which may be derivatized with alkyl groups having up to 3 carbon atoms and/or alkoxy groups having up to 3 carbon atoms; a tetralin ring which is bonded in the alpha or beta position and which may be derivatized with alkyl groups having up to 3 carbon atoms and/or alkoxy groups having up to 3 carbon atoms; a phenyl ring which may be derivatized with alkyl groups which contain up to 4 carbon atoms and/or with up to three groups of the structure Z-X in which Z is oxygen or sulfur and X is hydrogen, methyl, ethyl, n-propyl, i-propyl or tert-butyl; and a chroman system which is derivatized with up to 5 alkyl groups which contain up to 3 carbon atoms;

R1 is a group of the structure A-B-poly in which A is —(CH$_2$)$_n$—, n is an integer from 1 to 7, B is selected from the group consisting of: a bond; —CO—NH—; N(Y)—CO— wherein Y=H, CH$_3$ or C$_2$H$_5$; —CO—O—; —O—CO—; —SO$_2$—NH—; —S—S—; —S—; —O—; and —N(Y)— wherein Y=H, CH$_3$ or C$_2$H$_5$; and poly is a polymer having a molecular weight of up to 75000 selected from the group consisting of polyethylene glycol; polysaccharide; a gelatin partial hydrolysate which may be crosslinked; and a copolymer of acrylic acid and polyethylene glycol with a crosslinker; and R2 and R3 can be identical or different and are selected from the group consisting of an alkyl group with up to 4 carbon atoms or together form a ring and may be derivatized with a hydroxyl group or a hydroxyalkyl group, where the hydroxyalkyl group may be esterified and contains up to 3 carbon atoms, and their physiologically acceptable salts; and C* is in the R or S structure.

2. A compound as claimed in claim 1, where in C* is in the R structure.

3. A compound as claimed in claim 1, in which R' is β-naphthyl, A is —CH$_2$—, B is —CO—NH—, and poly is a polyethylene glycol with a molecular weight of 750 to 20000, and R2 and R3 together are piperidine.

4. A compound as claimed in claim 1, in which R' is β6,7-dimethoxynaphthyl, A is —CH$_2$—, B is —CO—NH—, and poly is a polyethylene glycol with a molecular weight of 750 to 20000, and R2 and R3 together are piperidine.

5. A compound as claimed in claim 1, in which R' is β-tetralinyl.

6. A compound as claimed in claim 1, in which R' is 4-methoxy-2,3,6-trimethylphenyl.

7. A compound as claimed in claim 1, in which R' is 2,2,5,7,8-pentamethylchromanyl.

8. A compound as claimed in claim 1, wherein B is —N(Y)—CO— with Y being H, CH$_3$, or C$_2$H$_5$.

9. A diagnostic or therapeutic composition containing a compound as claimed in claim 1.

10. A method of treating a host in need of an antithrombotic agent comprising administering to said host a compound as claimed in claim 1 or a pharmaceutical composition containing a compound as claimed in claim 1.

11. The compound as claimed in claim 1, wherein R2 and/or R3 is an esterified hydroxyalkyl which has been esterified with a carboxylic acid containing up to 17 carbon atoms.

\* \* \* \* \*